(12) United States Patent
Tegg et al.

(10) Patent No.: US 8,905,973 B2
(45) Date of Patent: Dec. 9, 2014

(54) HEMOSTASIS VALVE WITH ROLLER SEAL

(71) Applicant: St. Jude Medical, Atrial Fibrillation Division, Inc., St. Paul, MN (US)

(72) Inventors: Troy T. Tegg, Elk River, MN (US); Kevin Dillon, Chanhassen, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 13/748,117

(22) Filed: Jan. 23, 2013

(65) Prior Publication Data

US 2014/0207070 A1  Jul. 24, 2014

(51) Int. Cl.
*A61M 5/178* (2006.01)
*A61B 17/34* (2006.01)
*A61M 39/06* (2006.01)

(52) U.S. Cl.
CPC ........ *A61B 17/3498* (2013.01); *A61M 39/0606* (2013.01)
USPC .................................. 604/167.03; 604/167.05

(58) Field of Classification Search
USPC ............................ 604/164.01, 167.01–167.06
See application file for complete search history.

(56) References Cited

U.S. PATENT DOCUMENTS

| | | | |
|---|---|---|---|
| 7,081,106 B1 | 7/2006 | Guo et al. | |
| 7,105,009 B2 * | 9/2006 | Johnson et al. | 606/205 |
| 7,727,255 B2 * | 6/2010 | Taylor et al. | 606/205 |
| 7,914,515 B2 | 3/2011 | Heideman et al. | |
| 8,021,339 B2 * | 9/2011 | Rockrohr et al. | 604/167.04 |
| 2004/0167559 A1 | 8/2004 | Taylor et al. | |
| 2005/0085774 A1 | 4/2005 | Streifinger et al. | |

FOREIGN PATENT DOCUMENTS

| | | |
|---|---|---|
| WO | 02/087682 | 11/2002 |
| WO | 02087682 | 11/2002 |
| WO | 03/015848 | 2/2003 |
| WO | 03015848 | 2/2003 |
| WO | 2004/035108 | 4/2004 |
| WO | 2004035108 | 4/2004 |

OTHER PUBLICATIONS

International Search Report and Written Opinion for PCT/US2014/011968 mailed on Jun. 6, 2014; 11 pages.
International Search Report and Written Opinion in PCT Application No. PCT/US2012/011968 (Jun. 6, 2014).

* cited by examiner

*Primary Examiner* — Theodore Stigell
(74) *Attorney, Agent, or Firm* — Dykema Gossett PLLC

(57) ABSTRACT

A hemostasis valve has a housing having proximal and distal ends defining proximal and distal openings configured for passage of a medical device therethrough. The housing further defines a cavity between the proximal and distal ends. One or more rollers are received within the cavity and define end sections and a central section having a smaller diameter than the end sections. Sleeves are disposed about the rollers and are elastically deformable to form a fluid seal around the device. The sleeves each assume a first form when the device is absent from the cavity wherein a radially inner surface of the sleeve is located at a first distance from the central section of a roller and a second form when the device is present in the cavity wherein the surface is located at a second distance, less than the first distance, from the central section of the roller.

19 Claims, 9 Drawing Sheets

HEMOSTASIS VALVE WITH ROLLER SEAL

BACKGROUND a. Field

This disclosure relates to a hemostasis valve. In particular, the disclosure relates to a hemostasis valve that enables insertion of catheters and other medical devices into an introducer sheath, and removal of the devices from the sheath, with relatively little force while maintaining a fluid tight seal.

b. Background

A wide variety of medical devices are inserted into the body to diagnose and treat various medical conditions. Catheters, for example, are used to perform a variety of tasks within human bodies and other bodies including the delivery of medicine and fluids, the removal of bodily fluids and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

Conventional sheaths have a hemostasis valve at a proximal end of the sheath. The hemostasis valve allows for the introduction of catheters, guide wires and other medical devices into and through the sheath while preventing blood and other fluids from exiting. The valve also allows for removal of the devices while preventing air from entering the vasculature. The valve provides a seal around the medical device. In a conventional hemostasis valve, the seal is formed by one or more gaskets having a shaped slit through which the device passes. The frictional force applied by the gasket(s) to the medical device requires a relatively high amount of force to overcome. As a result, controlled insertion of the medical device is difficult.

BRIEF SUMMARY

The present disclosure relates to a hemostasis valve. In particular, the present disclosure relates to a hemostasis valve that that enables insertion of catheters and other medical devices into an introducer sheath, and removal of the devices from the sheath, with relatively little force while maintaining a fluid tight seal.

A hemostasis valve in accordance with one embodiment of the present disclosure includes a housing having a proximal end defining a proximal opening and a distal end defining a distal opening. The proximal and distal openings are configured for passage of a medical device therethrough. The housing further defines a cavity between the proximal and the distal ends. The valve further includes a roller configured to be received within the cavity and configured for rotation about an axis. The roller defines first and second axial end sections and a central section intermediate the first and second axial end sections. The central section may have a diameter smaller than a diameter of each of the first and second axial end sections. For example, the roller may taper from each of the first and second axial end sections towards an axial midpoint of the central section and may further define a concave surface between the first and second axial end sections. The valve further includes a sleeve disposed about the roller. The sleeve is elastically deformable. The sleeve is configured to assume a first form when the medical device is absent from the cavity wherein a radially inner surface of the sleeve is located at a first distance from the central section of the roller. The sleeve is also configured to assume a second form when the medical device is present in the cavity wherein the radially inner surface of the sleeve is located at a second distance from the central section of the roller, the second distance less than the first distance.

A hemostasis valve in accordance with another embodiment of the present disclosure includes a housing having a proximal end defining a proximal opening and a distal end defining a distal opening. The proximal and distal openings are configured for passage of a medical device therethrough. The housing further defines a cavity between the proximal and the distal ends. The valve further includes means, disposed within the cavity, for establishing a fluid seal both when the medical device is absent from the cavity and around the medical device when the medical device is present within the cavity. In one embodiment, the means may include a first roller configured to be received within the cavity and configured for rotation about a first axis. The first roller defines first and second axial end sections and a central section intermediate the first and second axial end sections. The central section may have a diameter smaller than a diameter of each of the first and second axial end sections. The means may further include a first sleeve disposed about the first roller. The first sleeve is elastically deformable and configured to assume a first form when the medical device is absent from the cavity wherein a radially inner surface of the first sleeve is located at a first distance from the central section of the first roller and a second form when the medical device is present in the cavity wherein the radially inner surface of the first sleeve is located at a second distance from the central section of the first roller, the second distance less than the first distance. The means may further include a second roller configured to be received within the cavity and configured for rotation about a second axis. The second roller defines first and second axial end sections and a central section intermediate the first and second axial end sections of the second roller. The central section of the second roller may have a diameter smaller than a diameter of each of the first and second axial end sections of the second roller. The means may further include a second sleeve disposed about the second roller. The second sleeve is elastically deformable and configured to assume a first form when the medical device is absent from the cavity wherein a radially inner surface of the second sleeve is located at a third distance from the central section of the second roller and a second form when the medical device is present in the cavity wherein the radially inner surface of the second sleeve is located at a fourth distance from the central section of the second roller, the fourth distance less than the third distance.

An introducer in accordance with one embodiment of the present disclosure includes a tubular sheath having proximal and distal ends. The introducer further includes a hemostasis valve disposed at the proximal end of the sheath. The valve includes a housing having a proximal end defining a proximal opening and a distal end defining a distal opening configured to receive a portion of the sheath. The proximal and distal openings are configured for passage of a medical device therethrough and into the sheath. The housing further defines a cavity between the proximal and distal ends. The valve further includes a roller configured to be received within the cavity and configured for rotation about an axis. The roller defines first and second axial end sections and a central section intermediate the first and second axial end sections. The central section may have a diameter smaller than a diameter of each of the first and second axial end sections. The valve further includes a sleeve disposed about the roller. The sleeve is elastically deformable and configured to assume a first form when the medical device is absent from the cavity wherein a radially inner surface of the sleeve is located at a first distance from the central section of the roller and a second form when the medical device is present in the cavity wherein the radially inner surface of the sleeve is located at a second distance from the central section of the roller, the second distance less than the first distance.

A hemostasis valve in accordance with the present teachings represents an improvement relative to conventional hemostasis valves. Because the seal formed by the rollers and sleeves moves with the device upon insertion and removal of the medical device, less force is required to insert and remove the device. As a result, it is easier to control insertion of the device.

The foregoing and other aspects, features, details, utilities, and advantages of the present disclosure will be apparent from reading the following description and claims, and from reviewing the accompanying drawings.

DETAILED DESCRIPTION

Figure 1:
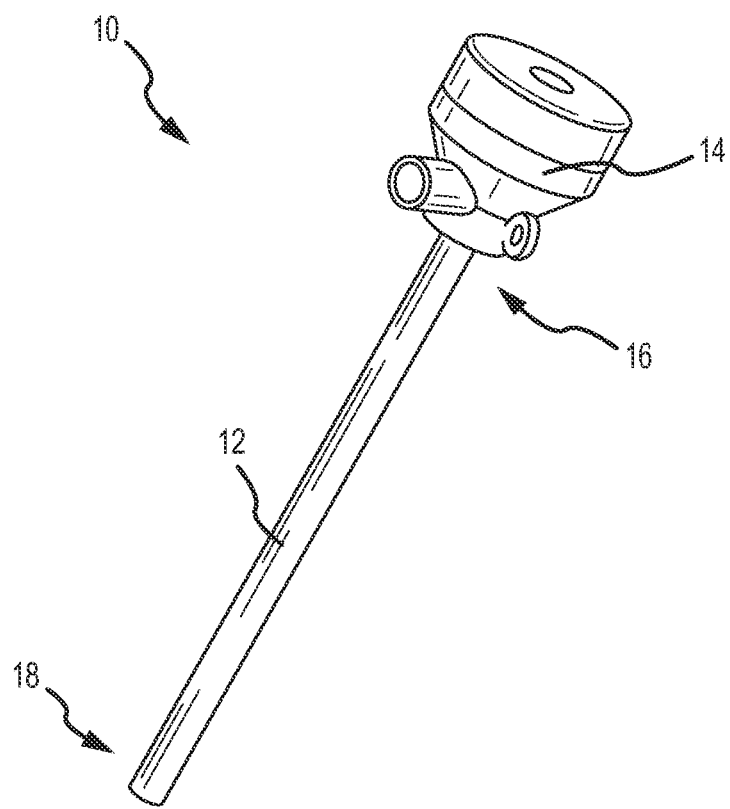
FIG. 1 is a perspective of an introducer including a hemostasis valve in accordance with one embodiment of the present teachings.
Figure 2:
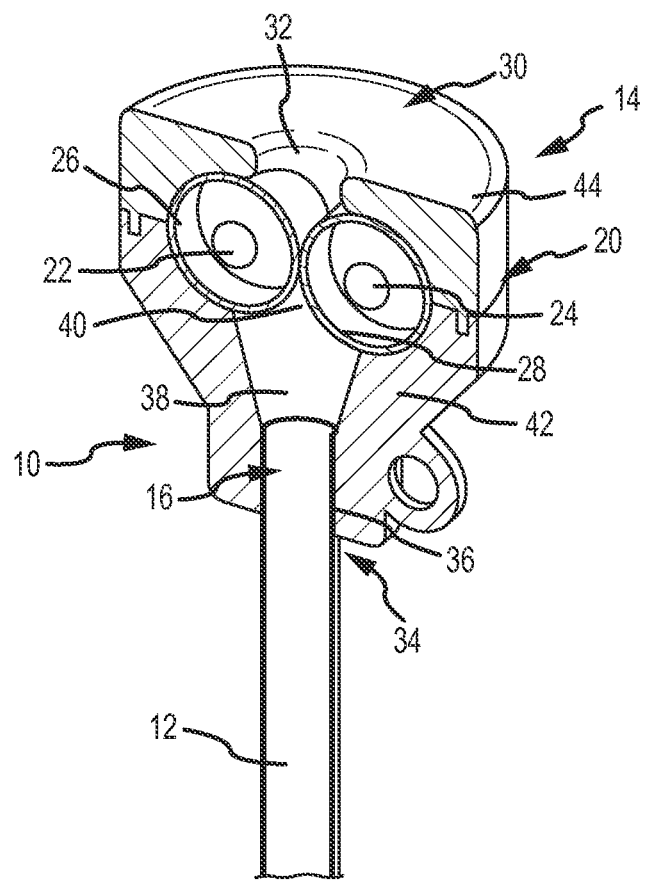
FIG. 2 is a cross-sectional view of the hemostasis valve of FIG. 1.

Referring now to the drawings wherein like reference numerals are used to identify identical components in the various views, FIGS. 1-2 illustrate one embodiment of an introducer 10 in accordance with the present disclosure. Introducer 10 is provided to facilitate the introduction of medical devices such as catheters, guide wires and the like into the vasculature of a body, to protect blood vessels and/or other anatomical structures as the medical devices are guided and manipulated to a region of interest within the body, and to minimize loss of blood during exchange of devices. Introducer 10 may be used, for example, with a deformable catheter of the type used to allow removal of bodily fluids or injection of fluids and medicine into the body and/or for transporting surgical tools or instruments within the body including those used for pacing or tissue ablation of the heart. The catheter may, for example, comprise an electrophysiology (EP) mapping catheter for use in gathering EP data associated with the heart to enable generation of an image of the geometry of the heart surface and related EP data. The catheter may alternatively comprise an intracardiac echocardiography (ICE) catheter used to generate an image of a region of interest within the body such as the heart. The catheter may alternatively comprise an ablation catheter used to ablate tissue within the heart to treat abnormal heart rhythms such as atrial fibrillation, ventricular tachycardia and similar conditions. Such catheters will typically include an elongate, flexible, tubular shaft configured for movement within the body. The shaft may be made from conventional materials such as polyurethane and defines one or more lumens configured to house and/or transport electrical conductors, fluids, or surgical tools. The shaft may support electrodes and position sensors, associated conductors, and possibly additional electronics used for signal processing or conditioning. The shaft may also permit transport, delivery, and/or removal of fluids (including irrigation fluids and bodily fluids), medicines, and/or surgical tools or instruments. Introducer 10 may include a sheath 12 and a hemostasis valve 14. Introducer 10 may further include a handle (not shown) to guide or steer sheath 12 as sheath 12 is maneuvered within the body. The handle may define a lumen coaxially aligned with sheath 12 as well as additional lumens for passage of conductors and fluids to or from electrical and fluid connectors.

Sheath 12 is configured to guide a medical device such as a catheter or guide wire to a target region within a body while protecting vessel walls and other anatomical structures. Sheath 12 has a deformable, elongate, tubular body having a proximal end 16 near valve 14 and a distal end 18 defining a distal tip (as used herein, the term "proximal" refers generally to a direction toward the end of a medical device nearer the clinician and further from the region of interest in the body where diagnosis or treatment takes place and the term "distal" refers to a direction towards the end of the medical device further away from the clinician and nearer to the region of interest where diagnosis or treatment takes place). Sheath 12 may include a tubular, polymeric inner liner, a braided wire layer for torque transfer, and an outer polymeric jacket. The inner liner may be made from a polymeric material such as polyfluoroethylene (PTFE), polyether block amides, nylon or thermoplastic elastomers such as the elastomer sold under the registered trademark "PEBAX" by Arkema, Inc. and defines a lumen extending from proximal end 16 to distal end 18 of sheath 12 that is configured to receive a catheter or other medical device therein. The braided wire layer is configured to provide appropriate levels of pushability, torqueability, flexibility, and kink resistance to sheath 12 and may be formed from stainless steel wire, preferably flat wire (wire having a cross-section that, when taken along the wire's longitudinal axis and measured along two orthogonal axes, is substantially rectangular) arranged in various braid patterns including one-over-one (involving at least two wires) or two-over-two (involving at least four wires) crossover patterns and having a pics (or "picks") per inch density between 5 and 100. The wire may be coated with a layer of an insulating material. The wire braid may be directly wound about the liner or placed on a core that is slid over the liner. The outer jacket may be made from a polymeric material such as polyfluoroethylene (PTFE), polyether block amides, nylon or thermoplastic elastomers such as the elastomer sold under the registered trademark "PEBAX" by Arkema, Inc. and may be extruded over the braided wire layer. Additional details regarding several exemplary sheath constructions may be found in commonly assigned U.S. Pat. No. 7,914,515 titled "Catheter and Introducer Catheter Having Torque Transfer Layer and Method of Manufacture," the entire disclosure of which is incorporated herein by reference.

Hemostasis valve 14 enables the introduction of catheters, guide wires and other medical devices into and through the sheath 12 while preventing blood and other fluids from exiting. Valve 14 also allows for removal of the devices while preventing air from entering the vasculature. Valve 14 may include a housing 20, rollers 22, 24, and sleeves 26, 28.

Housing 20 provides structural support to the other components of valve 14. Housing 20 also prevents foreign objects or elements from reaching those components and retains blood and other bodily fluids that may travel between sheath 12 and the medical device contained therein. Housing 20 may be made from conventional plastics including relatively rigid thermoplastics such as high-density polyethylene or an acrylonitrile-butadiene-styrene copolymer. Referring to FIG. 2, housing 20 includes a proximal end 30 defining a proximal opening 32 and a distal end 34 defining a distal opening 36. Housing 20 further defines a longitudinal passage 38 extending between openings 32, 36. Openings 32, 36 and passage 38 are configured for passage of a catheter, guide wire, or other medical device therethrough. Passage 38 opens into, and extends through, a cavity 40 defined in housing 20 between ends 30, 34 that is configured to receive rollers 22, 24 and sleeves 26, 28. Housing 20 may include a hub 42 and a cap 44.

Figure 3:
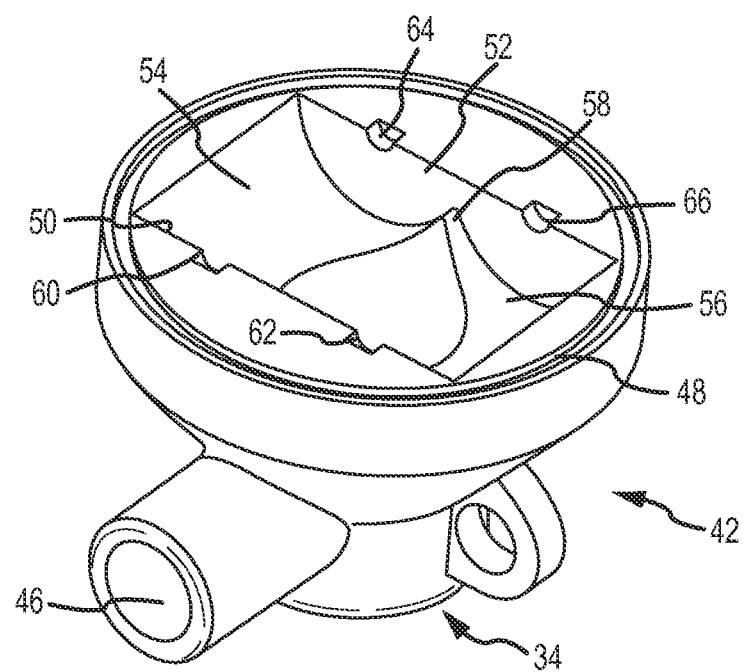
FIG. 3 is a perspective view of one portion of the housing of the hemostasis valve of FIG. 1.

FIG. 3 is a perspective view of one portion of the body 20 of the hemostasis valve 14 of FIG. 1. As can be further seen in FIG. 3, hub 42 defines the distal end 34 of housing 20. The distal opening 36 formed in distal end 34 is configured to receive the proximal end 16 of sheath 12 therein. End 16 of sheath 12 may be secured within opening 36 using a suitable technique such as heat adhesion or ultrasonic welding. Housing 20 may define a side port 46 to provide for the perfusion and aspiration of fluids through sheath 12. An annular groove 48 at the proximal end of hub 42 is configured to receive cap 44. Hub 42 defines one half of cavity 40 (the other half of cavity 40 being defined by cap 44). In particular, hub 42 includes a pair of opposed flat end walls 50, 52 and a pair of adjacent concave walls 54, 56 extending between end walls 50, 52 that together form two adjacent semicircular recesses configured to receive rollers 22, 24. Walls 54, 56 together define a central ridge 58 separating the recesses that extends from each end wall 50, 52, but is interrupted by passage 38. Additional semicircular walls 60, 62 and 64, 66 are formed on opposite side of end walls 50, 52 relative to walls 54, 56 and are configured to receive portions of rollers 22, 24 for a purpose described hereinbelow.

Figure 4:
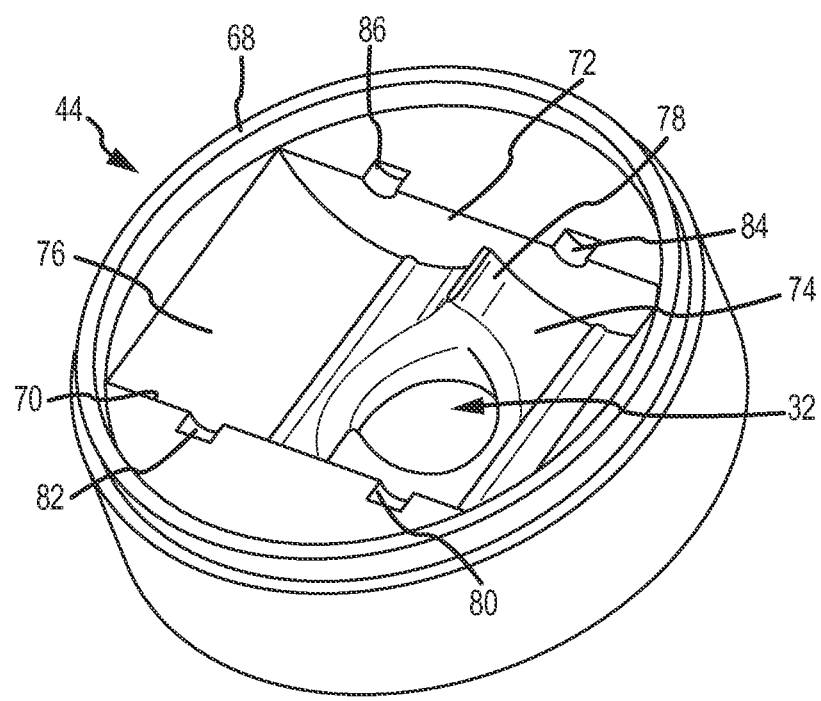
FIG. 4 is a perspective view of another portion of the housing of the hemostasis valve of FIG. 1.

Referring to FIG. 4, cap 44 defines the proximal end 30 of housing 20. The proximal opening 32 formed in proximal end 30 is configured to receive a catheter or similar medical device therein. Cap 44 defines an annular flange 68 disposed radially inward of an outer circumference of cap 44 and configured to be received within groove 48 of hub 42 to couple cap 44 to hub 42. Cap 44 may be secured to hub through ultrasonic welding or adhesives or an interference fit. Cap 44 defines one half of cavity 40 (the other half of cavity 40 being defined by hub 42). The portion of the cavity 40 in cap 44 is essentially a mirror image of the portion the cavity 40 in hub 42. As such, hub 44 includes a pair of opposed flat end walls 70, 72 aligned with end walls 50, 52 in hub 42 and a pair of adjacent concave walls 74, 76 extending between end walls 70, 72 that together form two adjacent semicircular recesses configured to receive rollers 22, 24. Walls 74, 76 together define a central ridge 78 separating the recesses that extends from each end wall 70, 72, but is interrupted by passage 38. Additional semicircular walls 80, 82 and 84, 86 are formed on opposite sides of end walls 70, 72 relative to walls 74, 76 and are aligned with walls 60, 62 and 64, 66 and configured to receive portions of rollers 22, 24 for a purpose described hereinbelow.

Figure 5:
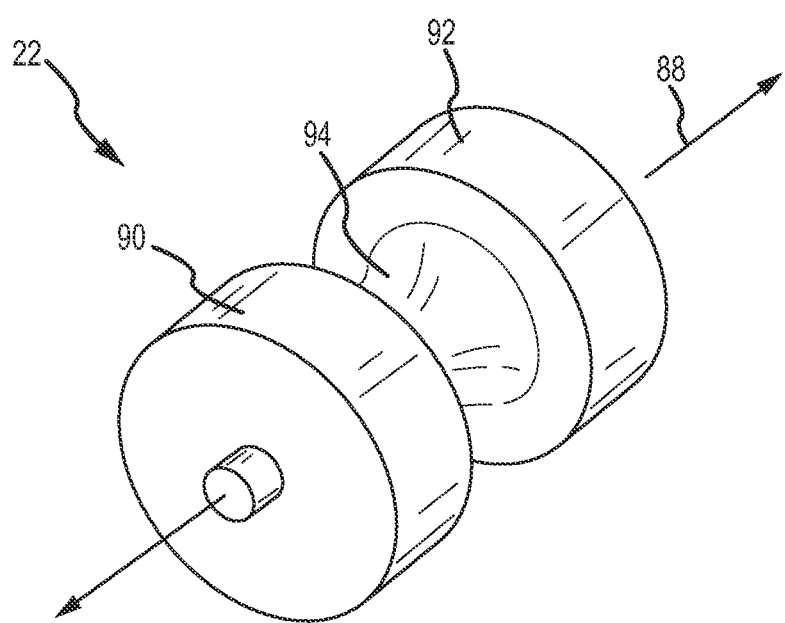
FIG. 5 is a perspective view of a roller of the hemostasis valve of FIG. 1.
Figure 7:
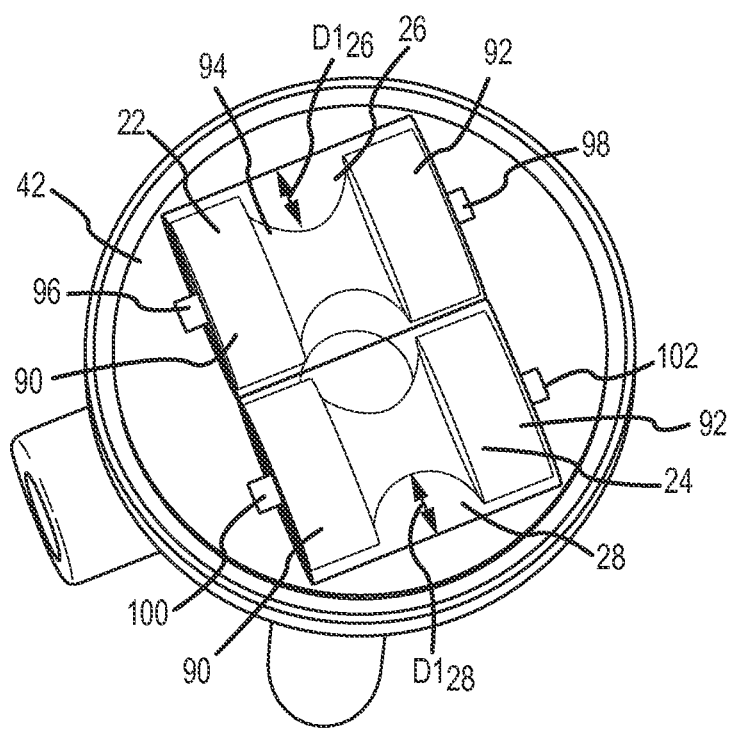
FIG. 7 is a perspective view of a portion of the hemostasis valve of FIG. 1 illustrating the position of the valve in the absence of a medical device.

Rollers 22, 24, provide a means for rotating sleeves 26, 28 and may be identical to one another. Rollers 22, 24, may be made from conventional plastics. Referring to FIG. 5, roller 22 is configured for rotation about an axis 88 (roller 24 is configured for rotation about an axis parallel to axis 88) and configured to be received within cavity 40. Each of rollers 22, 24 defines axial end sections 90, 92 and a central section 94 intermediate end sections 90, 92. Referring to FIG. 7, the axial end sections 90, 92 of each roller 22, 24 define axially projecting axle stubs 96, 98 and 100, 102, respectively. Stub 96 is configured to be received within a stub receiving portion of cavity 40 defined by wall 60 of hub 42 and wall 80 of cap 44. Likewise, stubs 98, 100, 102 are configured to be received within stub receiving portions of cavity 40 defined by walls 64, 62, 66 of hub 42 and corresponding walls 84, 82, 86 of cap 44. Stubs 96, 98, 100, 102 permit free rotation of rollers 22, 24 within cavity 40. Referring again to FIG. 5, central section 94 has a diameter that is smaller than the diameter of axial end sections 90, 92. The diameter of central section 94 may also vary and, in some embodiments, may taper moving inward from each of axial end sections 90, 92 toward an axial midpoint of central section 94 where the diameter is the smallest. In this manner, the central sections 94 of each roller 22, 24 may define opposed concave surfaces 104, 106 (best shown in FIG. 8), between the axial end sections 90, 92 of each roller 22, 24. Each concave surface 104, 106 defines a recess configured to receive a corresponding medical device.

Figure 6:
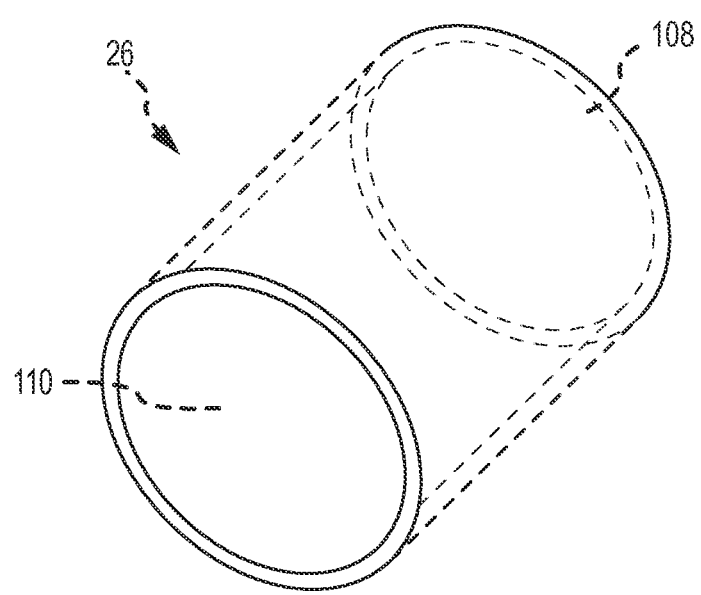
FIG. 6 is a perspective view of a sleeve of the hemostasis valve of FIG. 1.
Figure 8:
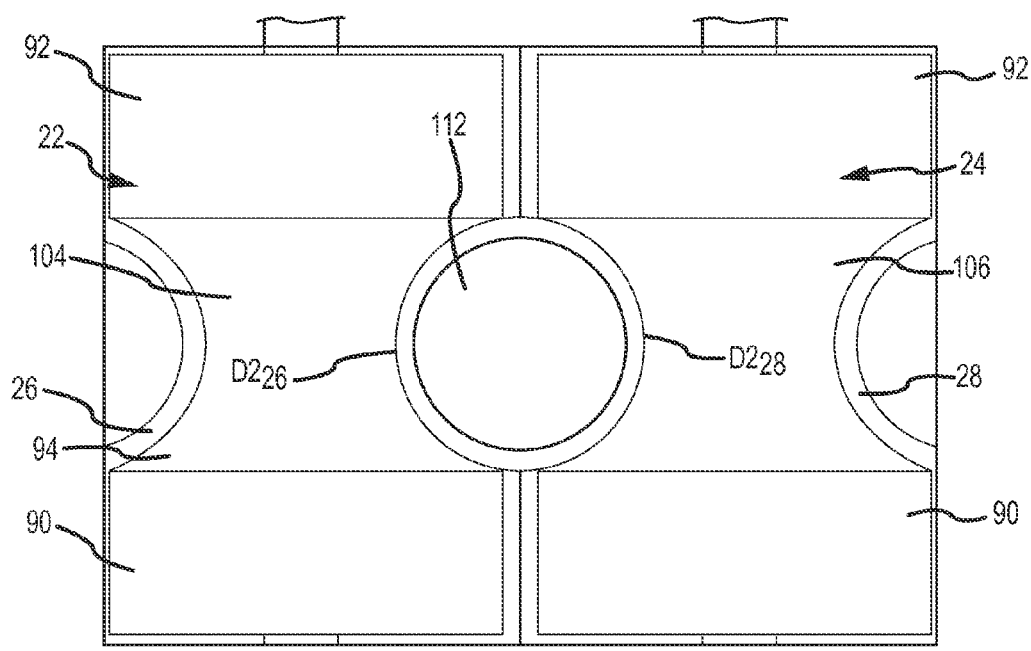
FIG. 8 is a view of the hemostasis valve of FIG. 1 illustrating the position of the valve in the presence of a medical device.

Referring again to FIG. 2, sleeves 26, 28 provide a seal around the catheter or other medical device inserted through housing 20. Sleeves 26, 28 may be made from silicon rubber or a thermoplastic elastomer. Sleeves 26, 28 are disposed about rollers 22, 24. Sleeves 26, 28 are elastically deformable and are configured to assume one form when a medical device is absent from cavity 40 and another form when a medical device is present in cavity 40. Referring to FIG. 6, in the absence of an external force, sleeves 26, 28 assume one form and, in particular, are cylindrical in shape defining radially outer and inner surfaces 108, 110. As a result, and with reference to FIG. 7, when a medical device is absent from cavity 40, sleeves 26, 28 engage one another over the full length of sleeves 26, 28 and form a fluid seal against egress of bodily fluids and the introduction of air in the vasculature. In particular, portions of the sleeve 26 covering the axial end sections 90, 92 of roller 22 engage corresponding portions of the sleeve 28 covering the axial end sections 90, 92 of roller 24 while the portion of the sleeve 26 covering the central section 94 of roller 22 engages a corresponding portion of the sleeve 28 covering the central section 94 of roller 22. The radially inner surface 110 of each sleeve 26, 28 is located at a distance $D1_{26}$, $D1_{28}$ from the axial midpoint of the central section 92 of a corresponding roller 22, 24. Referring to FIG. 8, when a medical device 112 is inserted through valve 14 and is present in cavity 40, sleeves 26, 28 assume another form and establish a fluid seal surrounding the device. When sleeves 26, 28 are in this form only the portions of the sleeve 26 covering the axial end sections 90, 92 of roller 22 engage corresponding portions of the sleeve 28 covering the axial end sections 90, 92 of roller 24. The portion of sleeve 26 covering the central section 94 of roller 22 is disengaged from the portion of sleeve 28 covering the central section 94 of roller 24. Further, the radially inner surface 110 of each sleeve 26, 28, is located at a distance $D2_{26}$, $D2_{28}$ (which may be zero (i.e. engagement between surface 110 and section 94) as shown in FIG. 8) from the axial midpoint of central section 94 of a corresponding roller 22, 24 that is less than the corresponding distance $D1_{26}$, $D1_{28}$. When the medical device 112 is removed from cavity 40, sleeves 26, 28 return to their original form. It should be noted that because sleeves 26, 28 are deformed in a radial direction rather than axial direction, valve 14 is better able to prevent the transmission of air into the vasculature. In accordance with another aspect of the present teachings, valve 14 may be adapted for use with medical devices of varying sizes (e.g., a guidewire and a catheter). In one embodiment, rollers 22, 24 may be biased towards one another by springs (not shown) or another biasing means. Adjustment of the spring force by, for example, repositioning of the springs, will facilitate the introduction of devices of varying diameter or size through the seal produced by rollers 22, 24 and sleeves 26, 28.

Figure 9:
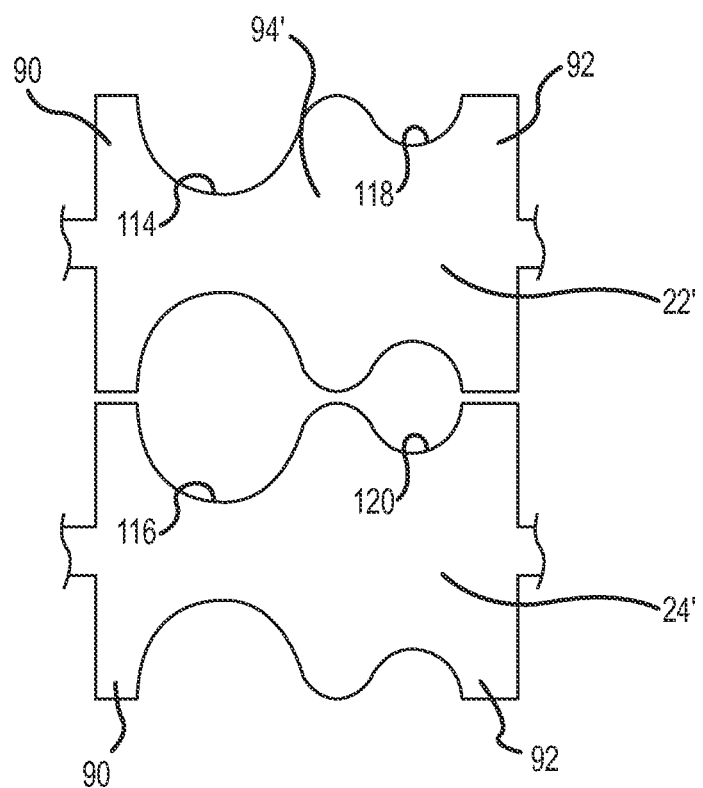
FIG. 9 is a plan view of two rollers for a hemostasis valve in accordance with another embodiment of the present teachings.

Referring to FIG. 9, in accordance with another embodiment, rollers 22', 24' may be provided that are substantially similar to rollers 22, 24 described hereinabove, but in which the diameter of central section 94' of each roller 22', 24' varies to define multiple recesses of different sizes configured to receive corresponding medical devices having different sizes. In particular, section 94' of each roller 22', 24' may define opposed concave surfaces 114, 116 and 118, 120, respectively, of varying depth between the axial end sections 90, 92 of each roller 22', 24'. Surfaces 114, 116 may be configured to receive a medical device having one size while surfaces 118, 120 may be configured to receive a medical device of a different, smaller, size. For example, surfaces 118, 120 may be configured to receive a guidewire while surfaces 114, 116 may be configured to receive a catheter. In one example embodiment, surfaces 118, 120 are configured in size and shape to receive a 0.014 inch guidewire whereas surfaces 114, 116 are configured in size and shape to receive a 7.5 Fr catheter. Other configurations are also possible. Rollers 22', 24' may be shifted in either axial direction along their rotational axes to move corresponding surfaces 114, 116 or 118, 120 to a center position within housing 20 and into alignment with openings 32, 36 and passage 38.

A hemostasis valve 14 in accordance with the present teachings represents an improvement relative to conventional hemostasis valves because less force is required to insert and/or remove a medical device from introducer 10. In particular, rollers 22, 24 and sleeves 26, 28 provide a seal that moves with the device as it is inserted or removed while maintaining a fluid seal around the device thereby reducing frictional force opposing movement of the device. Easier insertion and removal of the device permits more controlled movement for the clinician.

Although several representative embodiments have been described above with a certain degree of particularity, those skilled in the art could make numerous alterations to the disclosed embodiments without departing from the scope of the disclosed embodiments. All directional references (e.g., upper, lower, upward, downward, left, right, leftward, rightward, top, bottom, above, below, vertical, horizontal, clockwise and counterclockwise) are only used for identification purposes to aid the reader's understanding of the disclosed embodiments, and do not create limitations, particularly as to the position, orientation, or use of the embodiments. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the embodiments as defined in the appended claims.

What is claimed is:

1. A hemostasis valve, comprising:
   a housing having a proximal end defining a proximal opening and a distal end defining a distal opening, said proximal and distal openings configured for passage of a medical device therethrough, said housing further defining a cavity between said proximal and said distal ends;
   a first roller configured to be received within said cavity and configured for rotation about a first axis, said first roller defining first and second axial end sections and a central section intermediate said first and second axial end sections, wherein an outer surface diameter of each of said first and second axial end sections is greater than an outer surface diameter of said central section; and,
   a first sleeve disposed about said first roller, said first sleeve comprising a radially inner surface and a radially outer surface, said radially inner surface nearer to said first axis than said radially outer surface, said radially inner surface of said first sleeve engages said outer surface of each of said first and second axial end sections, said first sleeve elastically deformable and configured to assume a first form when the medical device is absent from said cavity wherein said radially inner surface of said first sleeve is located at a first distance from said central section of said first roller and a second form when the medical device is present in said cavity wherein said radially inner surface of said first sleeve is located at a second distance from said central section of said first roller, said second distance less than said first distance.

2. The hemostasis valve of claim 1 wherein said first roller tapers from each of said first and second axial end sections towards an axial midpoint of said central section.

3. The hemostasis valve of claim 1 wherein said first roller defines a concave surface between said first and second axial end sections.

4. The hemostasis valve of claim 1 further comprising:
   a second roller configured to be received within said cavity and configured for rotation about a second axis, said second roller defining first and second axial end sections and a central section intermediate said first and second axial end sections of said second roller; and,
   a second sleeve disposed about said second roller, said second sleeve elastically deformable and configured to assume a first form when the medical device is absent from said cavity wherein a radially inner surface of said second sleeve is located at a third distance from said central section of said second roller and a second form when the medical device is present in said cavity wherein said radially inner surface of said second sleeve is located at a fourth distance from said central section of said second roller, said fourth distance less than said third distance.

5. The hemostasis valve of claim 4 wherein said first and second axes are parallel to one another.

6. The hemostasis valve of claim 4 wherein, when the medical device is absent from said cavity, a first portion of said first sleeve covering said first axial end section of said first roller engages a first portion of said second sleeve covering said first axial end section of said second roller and a second portion of said first sleeve covering said central section of said first roller engages a second portion of said second sleeve covering said central section of said second roller and, when the medical device is present in said cavity, said first portion of said first sleeve engages said first portion of said second sleeve and said second portion of said first sleeve is disengaged from said second portion of said second sleeve.

7. The hemostasis valve of claim 1 wherein said central section of said first roller defines first and second recesses having different sizes.

8. A hemostasis valve, comprising:
a housing having a proximal end defining a proximal opening and a distal end defining a distal opening, said proximal and distal openings configured for passage of a medical device therethrough, said housing further defining a cavity between said proximal and distal ends;
a first roller configured to be received within said cavity and configured for rotation about a first axis, said first roller defining first and second axial end sections and a central section intermediate said first and second axial end sections, wherein an outer surface diameter of each of said first and second axial end sections is greater than an outer surface diameter of said central section; and
a first elastically deformable sleeve disposed about said first roller that includes an inner surface, wherein portions of said inner surface are engaged with an outer surface of each of said first and second axial end sections and a portion of said inner surface is disengaged from the central section, wherein said first roller and said first elastically deformable sleeve establish a fluid seal both when the medical device is absent from said cavity and along the medical device when the medical device is present within said cavity.

9. The hemostasis valve of claim 8 wherein said fluid seal further comprises:
a radially outer surface disposed on said first elastically deformable sleeve, said radially inner surface nearer to said first axis than said radially outer surface, said first elastically deformable sleeve configured to assume a first form when the medical device is absent from said cavity wherein said radially inner surface of said first sleeve is located at a first distance from said central section of said first roller and a second form when the medical device is present in said cavity wherein said radially inner surface of said first sleeve is located at a second distance from said central section of said first roller, said second distance less than said first distance;
a second roller configured to be received within said cavity and configured for rotation about a second axis, said second roller defining first and second axial end sections and a central section intermediate said first and second axial end sections of said second roller; and,
a second sleeve disposed about said second roller, said second sleeve elastically deformable and configured to assume a first form when the medical device is absent from said cavity wherein a radially inner surface of said second sleeve is located at a third distance from said central section of said second roller and a second form when the medical device is present in said cavity wherein said radially inner surface of said second sleeve is located at a fourth distance from said central section of said second roller, said fourth distance less than said third distance.

10. The hemostasis valve of claim 9 wherein said first roller tapers from each of said first and second axial end sections of said first roller towards an axial midpoint of said central section of said first roller and said second roller tapers from each of said first and second axial end sections of said second roller towards an axial midpoint of said central section of said second roller.

11. The hemostasis valve of claim 9 wherein said first roller defines a concave surface between said first and second axial end sections of said first roller and said second roller defines a concave surface between said first and second axial end sections of said second roller, said concave surfaces of said first and second roller oriented opposite to one another to define a circular passage for the medical device.

12. An introducer, comprising:
a tubular sheath having proximal and distal ends; and,
a hemostasis valve disposed at said proximal end of said sheath, said valve comprising:
a housing having a proximal end defining a proximal opening and a distal end defining a distal opening configured to receive a portion of said sheath, said proximal and distal openings configured for passage of a medical device therethrough and into said sheath, said housing further defining a cavity between said proximal and distal ends;
a first roller configured to be received within said cavity and configured for rotation about a first axis, said first roller defining first and second axial end sections and a central section intermediate said first and second axial end sections, wherein an outer surface diameter of each of said first and second axial end sections is greater than an outer surface diameter of said central section; and,
a first sleeve disposed about said first roller, said first sleeve comprising a radially inner surface and a radially outer surface, said radially inner surface nearer to said first axis than said radially outer surface, said radially inner surface of said first sleeve engages said outer surface of each of said first and second axial end sections, said first sleeve elastically deformable and configured to assume a first form when the medical device is absent from the cavity wherein said radially inner surface of said first sleeve is located at a first distance from said central section of said first roller and a second form when the medical device is present in the cavity wherein the radially inner surface of said first sleeve is located at a second distance from said central section of said first roller, said second distance less than said first distance.

13. The introducer of claim 12 wherein said central section of said first roller has a diameter smaller than a diameter of each of said first and second axial end sections of said first roller.

14. The introducer of claim 12 wherein said first roller tapers from each of said first and second axial end sections towards an axial midpoint of said central section.

15. The introducer of claim 12 wherein said first roller defines a concave surface between said first and second axial end sections.

16. The introducer of claim 12, further comprising:
a second roller configured to be received within said cavity and configured for rotation about a second axis, said second roller defining first and second axial end sections and a central section intermediate said first and second axial end sections of said second roller; and,
a second sleeve disposed about said second roller, said second sleeve elastically deformable and configured to assume a first form when the medical device is absent from said cavity wherein a radially inner surface of said second sleeve is located at a third distance from said central section of said second roller and a second form when the medical device is present in said cavity wherein said radially inner surface of said second sleeve is located at a fourth distance from said central section of said second roller, said fourth distance less than said third distance.

17. The introducer of claim 16 wherein said first and second axes are parallel to one another.

18. The introducer of claim 16 wherein, when the medical device is absent from said cavity, a first portion of said first sleeve covering said first axial end section of said first roller engages a first portion of said second sleeve covering said first axial end section of said second roller and a second portion of said first sleeve covering said central section of said first roller engages a second portion of said second sleeve covering said central section of said second roller and, when the medical device is present in said cavity, said first portion of said first sleeve engages said first portion of said second sleeve and said second portion of said first sleeve is disengaged from said second portion of said second sleeve.

19. The introducer of claim 12 wherein said central section of said first roller defines first and second recesses having different sizes.

\* \* \* \* \*